United States Patent
Hampe et al.

(10) Patent No.: US 11,316,302 B2
(45) Date of Patent: Apr. 26, 2022

(54) ELECTRICAL PLUG-IN CONNECTION FOR A MEDICAL DEVICE ARRANGEMENT

(71) Applicant: Drägerwerk AG & Co. KGaA, Lübeck (DE)

(72) Inventors: Markus Hampe, Lübeck (DE); Markus Kämer, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

(21) Appl. No.: 17/155,488

(22) Filed: Jan. 22, 2021

(65) Prior Publication Data
US 2021/0234308 A1 Jul. 29, 2021

(30) Foreign Application Priority Data
Jan. 24, 2020 (DE) .................... 10 2020 000 422.9

(51) Int. Cl.
*H01R 13/642* (2006.01)
*H01R 24/20* (2011.01)
*H01R 24/28* (2011.01)
*H01R 43/24* (2006.01)
*H01R 103/00* (2006.01)

(52) U.S. Cl.
CPC ........... *H01R 13/642* (2013.01); *H01R 24/20* (2013.01); *H01R 24/28* (2013.01); *H01R 43/24* (2013.01); *H01R 2103/00* (2013.01); *H01R 2201/12* (2013.01)

(58) Field of Classification Search
CPC ..... H01R 13/642; H01R 13/64; H01R 124/20
See application file for complete search history.

(56) References Cited

U.S. PATENT DOCUMENTS

| | | | | |
|---|---|---|---|---|
| 4,986,769 A * | 1/1991 | Adams, III | ............ | H01R 13/64 439/347 |
| 7,537,471 B2 * | 5/2009 | Teicher | .................. | H01R 13/64 439/172 |
| 8,647,156 B2 * | 2/2014 | Golko | .................... | H01R 25/00 439/668 |

(Continued)

FOREIGN PATENT DOCUMENTS

DE 102008039137 B3 2/2010
DE 202012008785 U1 11/2012

(Continued)

*Primary Examiner* — Neil Abrams
(74) *Attorney, Agent, or Firm* — McGlew and Tuttle, P.C.

(57) ABSTRACT

An electrical plug-in connection (100) provides a positive connection of a plug-in element (110) to a receiving element (120) within a medical device arrangement (700). The plug-in element forms a male part with an insertion area (112). The receiving element forms a female part with a receptacle (122) corresponding to the insertion area. In a plugged-together state this provides an electrical connection between a plug-side cable (118) connected to the plug-in element and a receptacle-side cable (128) connected to the receiving element via at least two contact areas. The insertion area is 180° rotationally symmetrical relative to an insertion axis (140) of the electrical plug-in connection. The insertion axis is oriented to an insertion direction, whereby a pole reversal of the electrical plug-in connection is allowed without being mirror symmetrical in relation to a reference plane comprising the insertion axis.

14 Claims, 5 Drawing Sheets

(56) References Cited

U.S. PATENT DOCUMENTS

| | | | | |
|---|---|---|---|---|
| 8,882,524 B2* | 11/2014 | Golko | ................ | H01R 13/6273 |
| | | | | 439/218 |
| 8,998,632 B2* | 4/2015 | Golko | .................... | H01R 24/58 |
| | | | | 439/345 |
| 9,142,926 B2* | 9/2015 | Tsai | ................... | H01R 12/7076 |
| 9,478,918 B1* | 10/2016 | Yin | .................... | H01R 13/6315 |
| 2012/0276760 A1* | 11/2012 | Cho | ........................ | H01R 24/62 |
| | | | | 439/77 |
| 2021/0234308 A1* | 7/2021 | Hampe | ............. | A61M 16/0816 |

FOREIGN PATENT DOCUMENTS

| | | |
|---|---|---|
| DE | 102012103216 A1 | 10/2013 |
| DE | 102017000996 A1 | 8/2018 |

\* cited by examiner

ELECTRICAL PLUG-IN CONNECTION FOR A MEDICAL DEVICE ARRANGEMENT

CROSS REFERENCE TO RELATED APPLICATIONS

This application claims the benefit of priority under 35 U.S.C. § 119 of German Application 10 2020 000 422.9, filed Jan. 24, 2020, the entire contents of which are incorporated herein by reference.

TECHNICAL FIELD

The present invention pertains to an electrical plug-in connection for a positive-locking connection of a plug-in element to a receiving element within a medical device arrangement. Furthermore, the present invention pertains to an electrical plug-in connection system with at least two electrical plug-in connections according to the present invention as well as to a medical device arrangement with the electrical plug-in connection system according to the present invention.

TECHNICAL BACKGROUND

Electrical plug-in connections are known in a variety of forms and for a variety of applications. An electrical plug-in connection typically consists of a plug-in element that forms the male part of the electrical plug-in connection and of a receiving element that forms the female part of the electrical plug-in connection. An electrical connection is provided between the two elements by means of the electrical plug-in connection via corresponding contact areas at the two elements.

Furthermore, it is known to configure the plug-in element and the receiving element each as mirror-symmetrical in order to make possible a pole reversal of the plug-in connection and to simplify the handling of the plug-in connection in daily routine practice. The direction of the pole of an electrical connection plays no role especially for the common household alternating current.

For a system comprising a variety of electrical plug-in connections, it is often desirable in case of safety-relevant applications that a mixing up of a plurality of plug-elements or receiving elements with one another be avoided. For this purpose, it is known to associate a characteristic shape for the plug-in element and the receiving element with each electrical plug-in connection within such a system, which shape distinguishes this electrical plug-in connection from the other electrical plug-in connections within the system.

It may be particularly important especially for use within a medical device arrangement not to mix up plug-in elements of different electrical plug-in connections with one another in order not to put the safety of a patient to be supplied at risk.

SUMMARY

An object of the present invention is to provide an electrical plug-in connection for an electrical plug-in connection system, which allows a pole reversal by means of rotating the plug-in element and yet in the process advantageously prevents a mixing up of the plug-in elements.

According to a first aspect of the present invention, an electrical plug-in connection for the positive-locking connection of a plug-in element to a receiving element within a medical device arrangement is proposed according to the present invention for accomplishing this object.

In this connection, the plug-in element forms a male part of the electrical plug-in connection with an insertion area and the receiving element forms a female part of the electrical plug-in connection with a receptacle corresponding to the insertion area. Furthermore, in the plugged-together state, the plug-in element and the receiving element are configured to provide an electrical connection between a plug-side cable connected to the plug-in element and a receptacle-side cable connected to the receiving element via at least two contact areas. Further, the insertion area is configured to be rotationally symmetrical by 180° in relation to an insertion axis of the electrical plug-in connection, which insertion axis is oriented according to an insertion direction, as a result of which a pole reversal of the electrical plug-in connection is allowed. However, the insertion area according to the present invention is not mirror symmetrical in relation to any desired reference plane comprising the insertion axis.

It was found within the scope of the present invention that dispensing with a mirror-symmetrical configuration of the insertion area of the plug-in element reduces the probability of an accidental insertion of an unrelated plug-in element, since many commercially available plug-in elements have a mirror-symmetrical configuration. Furthermore, it was found that a pole reversal of the electrical plug-in connection is already made possible due to a rotational symmetry by 180°, i.e., especially a point symmetry, without a mirror symmetry of the insertion area being necessary for this.

A pole reversal is advantageously allowed due to the electrical plug-in connection according to the present invention, so that a user can plug together the two elements in an especially fast and simple manner, without checking the orientation of the insertion area for this.

Because of the simple structure, the electrical plug-in connection according to the present invention can be provided by simple parts manufactured, for example, within the framework of an injection molding process. Thus, no increased effort compared to the manufacture of known commercially available electrical plug-in connections is necessary.

Due to the absent mirror symmetry of the insertion area, this insertion area according to the present invention has a characteristic shape, by means of which an operating error by a user of the electrical plug-in connection is avoided. In particular, commercially available plug-in elements with a mirror-symmetrical configuration cannot or at least partly cannot be used in combination with the receiving element according to the present invention.

The characteristic shape of an insertion area according to the present invention does advantageously increase safety, since the two electrical components put together by the electrical plug-in connection were supplied by the same manufacturer or by manufacturers cooperating with one another. Hence, a compatibility of the two components is probable. As a result, an especially safe operation of the corresponding electrical system is guaranteed, which may advantageously lead to increased patient safety especially in the medical setting.

The at least two contact areas are preferably provided via at least two contact pins at one of the two elements of the electrical plug-in connection and corresponding pin receptacles at the corresponding other element. The two contact areas are in this case provided by means of a conductive material, especially by means of a metal. The provision of suitable materials and/or of suitable alloys for the creation of contact areas within an electrical plug-in connection is known to the person skilled in the art, so that details about the selection of materials and the manufacture will not be discussed below.

The insertion direction is the direction, in which the plug-in element has to be moved in order to insert the insertion area into the receptacle of the receiving element. In this case, the insertion axis is an axis oriented in the insertion direction, which axis runs through the insertion area and in the process forms the axis of symmetry, about which the insertion area is configured to be rotationally symmetrical by 180°. The insertion area according to the present invention is preferably correspondingly point symmetrical about the point at which the insertion axis intersects the insertion area.

The fastening of the plug-side and receptacle-side cables to the two elements takes place preferably in a manner known to the person skilled in the art of electrical plug-in connections, so that this will not be discussed in detail below.

The reference plane is any desired plane of the planes which comprise the insertion axis. According to the present invention, there is consequently no plane, to which the insertion area is configured as being mirror symmetrical.

Preferred embodiments of the plug-in connection according to the present invention will be described below.

According to the present invention, the insertion area has an essentially wave-shaped, z-shaped or s-shaped configuration. These shapes meet in an especially simple manner the condition according to the present invention that the insertion area has a point-symmetrical configuration, without in this case being mirror-symmetrical. Especially advantageously, the z-shape and the s-shape have each at the outer ends of the respective insertion area an area that prevents an accidental rotation, and in particular an unscrewing, of the plug-in element in the put-together state of the electrical plug-in connection. This increased securing against rotation ensures an especially reliable connection of the two elements of the plug-in connection according to the present invention. In the process, the Z-shape and S-shape form an especially angular and an especially curved example of the same basic shape. Wave-shaped may hence also be defined as zig-zag-shaped or tooth-shaped or the like in the sense of the present invention.

In a preferred embodiment, the receiving element has at least two contact pins which belong each to the respective contact area of the at least two contact areas. In this embodiment, at least two of the at least two contact pins are in this case arranged outside of the insertion axis. It is ensured via these contact pins located outside of the insertion axis that a pole reversal of the electrical plug-in connection is possible due to a rotation of the plug-in element and hence a corresponding rotation of the contact areas provided via the contact pins. In a variant of this embodiment, the electrical plug-in connection additionally has a contact area, which is arranged in the area of the insertion axis, for example, via another contact pin, especially via a third contact pin, in the area of the insertion axis. Different configurations of contact pins are known and will hence not be explained in detail below.

In another embodiment, the plug-in element and the receiving element have a respective grip area with a respective grip structure. Such a grip structure is advantageously configured with a structured surface, especially with an ergonomically shaped surface. As a result, the respective grip structure allows, in the case of poor vision as well, such an orientation of an angular position of the plug-in element and of the receiving element to one another that a plugging together is possible in a simple manner because of these grip structures coordinated with one another, especially without a detailed study of the structure of the insertion area being possible, especially being intuitively possible.

According to a second aspect of the present invention, an electrical plug-in connection system with at least two electrical plug-in connections according to at least one of the above embodiments is provided for accomplishing the above-mentioned object.

A first electrical plug-in connection of the at least two electrical plug-in connections has, compared with a second electrical plug-in connection of the at least two electrical plug-in connections, in this case a first insertion area that is mirror-inverted to a second insertion area of the second electrical plug-in connection.

The electrical plug-in connection system according to the present invention has the advantages of the electrical plug-in connection according to the first aspect of the present invention and in addition the advantage that the two plug-in elements cannot be inserted into the receptacle of the respective, unrelated receiving element in case of a mix-up by a user. Furthermore, the two plug-in elements of the electrical plug-in connection system can be immediately recognized because of their structural similarity as belonging to the same plug-in connection system. The structure of the two insertion areas is thus identical and only a mirrored shape, which prevents an accidental reinsertion of the plug-in element into the other respective receiving element, distinguishes the two insertion areas from one another.

In an especially preferred embodiment, the respective plug-in element with the respective plug-side cable forms a reusable component and the respective receiving element with the respective receptacle-side cable forms a disposable component of the electrical plug-in connection system. This embodiment is especially advantageous within a sterile setting since the plug-in element is typically simpler to clean than the receiving element. When one of the two components shall be reused, the plug-in element therefore represents the variant that is simpler to clean. In addition to hygienic aspects, the provision of a disposable component may also be advantageous because of a short life of corresponding electronic components or because of the low acceptance by the user of corresponding used components.

In another embodiment, the plug-side cables are each configured to connect the electrical plug-in connection system to a power supply unit. Furthermore, the receptacle-side cables are configured each to connect the electrical plug-in connection system to a device to be supplied with power. In a preferred variant of this embodiment, the receptacle-side cable together with the device to be supplied is configured as a disposable component, whereas the power supply unit with the plug-side cable is a reusable component.

In an advantageous embodiment of the electrical plug-in connection system the plug-in element and the receiving element of the first electrical plug-in connection are at least partly configured in a first color and the plug-in element and the receiving element of the second electrical plug-in connection are at least partly configured in a second color. In this embodiment, it is advantageously possible to readily infer that the receiving element and the plug-in element, respectively, belong to a common electrical plug-in connection because of the colors. In particular, insertion areas, which are similar because of the symmetrical configuration, need not be compared to one another.

In another embodiment according to the present invention, a respective plug-in element and the corresponding receiving element have a respective grip area with a respective grip structure. This grip structure advantageously has a characteristic configuration. Consequently, the respective grip structure also allows, in the case of poor vision, such an orientation of an angular position of the plug-in element and of the receiving element to one another that a plugging together is possible in a simple manner because of these grip structures coordinated with one another, especially without a detailed study of the structure of the insertion area being possible, especially being intuitively possible. In an especially preferred variant, the two grip structures of the two electrical plug-in connections differ markedly from one another such that first a contacting of a plug-in element with the non-corresponding receiving element is not intuitively attempted at all by a user because of the grip structures.

In another embodiment according to the present invention, the two insertion areas of the electrical plug-in connection are configured such that a test plug with a mirror-symmetrical configuration can be inserted into the two receiving elements of the at least two electrical plug-in connections and it allows an electrical connection between the test plug and the receiving element. In this case, the insertion area of the test plug has a smaller surface than the insertion area of the plug-in element according to the present invention. As a result, the maintenance of the electrical plug-in connection system is simplified, since a testing of the operability of the respective receiving element and of the respective devices connected thereto is possible due to a universally insertable test plug.

According to a third aspect of the present invention, a medical device arrangement with an electrical plug-in connection system according to one of the above embodiments is proposed for accomplishing the above-mentioned object.

The above-mentioned advantages of the electrical plug-in connection according to the first aspect of the present invention and of the electrical plug-in connection system according to the second aspect of the present invention are especially advantageously distinct for the medical device arrangement according to the third aspect of the present invention. Thus, a secure association between the plug-in element and the receiving element supports a secure and reliable operation of the medical device arrangement and thus the patient's safety.

Furthermore, a rapid operation of the electrical plug-in connection is advantageously possible even under poor light conditions due to the pole reversal allowable according to the present invention, which allows an especially rapid operation of the medical device arrangement according to the present invention.

Finally, the characteristic shape of the respective insertion area according to the present invention allows a secure association of the components of a manufacturer of the medical device arrangement. As a result, problems with the compatibility of components of different manufacturers are avoided. Thus, a safe use of the medical device arrangement is supported and thus patient safety is improved.

In a preferred embodiment of the medical device arrangement according to the present invention, a respective plug-in connection is associated with a respective heatable tube of a tube system of the medical device arrangement. In this case, a heater, especially a heater of a breathing gas humidifier, of the associated heatable tube is supplied with power via the respective plug-in connection. Since such a heater is typically embodied by a resistance wire, a pole reversal of the electrical plug-in connection is possible without an adverse effect on the operability of the corresponding medical device arrangement. In this embodiment, the prevention of a mixing up of the two plug-in elements of the two plug-in connections prevents in a preferred variant the inspiratory and expiratory heating ports for the corresponding inspiratory and expiratory ventilation tubes from being mixed up with one another. Since the inspiratory heating port is controlled electrically and the expiratory heating port is not controlled electrically, a reliable prevention of such a mix-up is especially advantageous for ensuring the operability of the medical device arrangement.

In an especially advantageous variant of the preceding embodiment the respective receiving element is connected non-detachably to the associated heatable tube via the respective receptacle-side cable. In this connection, the receiving element, the receptacle-side cable and the heatable tube preferably together form a disposable component of the medical device arrangement. Use is advantageously made in this variant of the fact that a ventilation tube is typically a disposable component in medical applications because of hygienic aspects. Since the plug-in element is especially simple to clean, it is hence advantageous to provide only the receptacle-side components as disposable components and to provide the plug-side components such that a simple cleaning and/or disinfection is possible.

The present invention shall now be explained in more detail on the basis of advantageous exemplary embodiments, which are schematically shown in the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
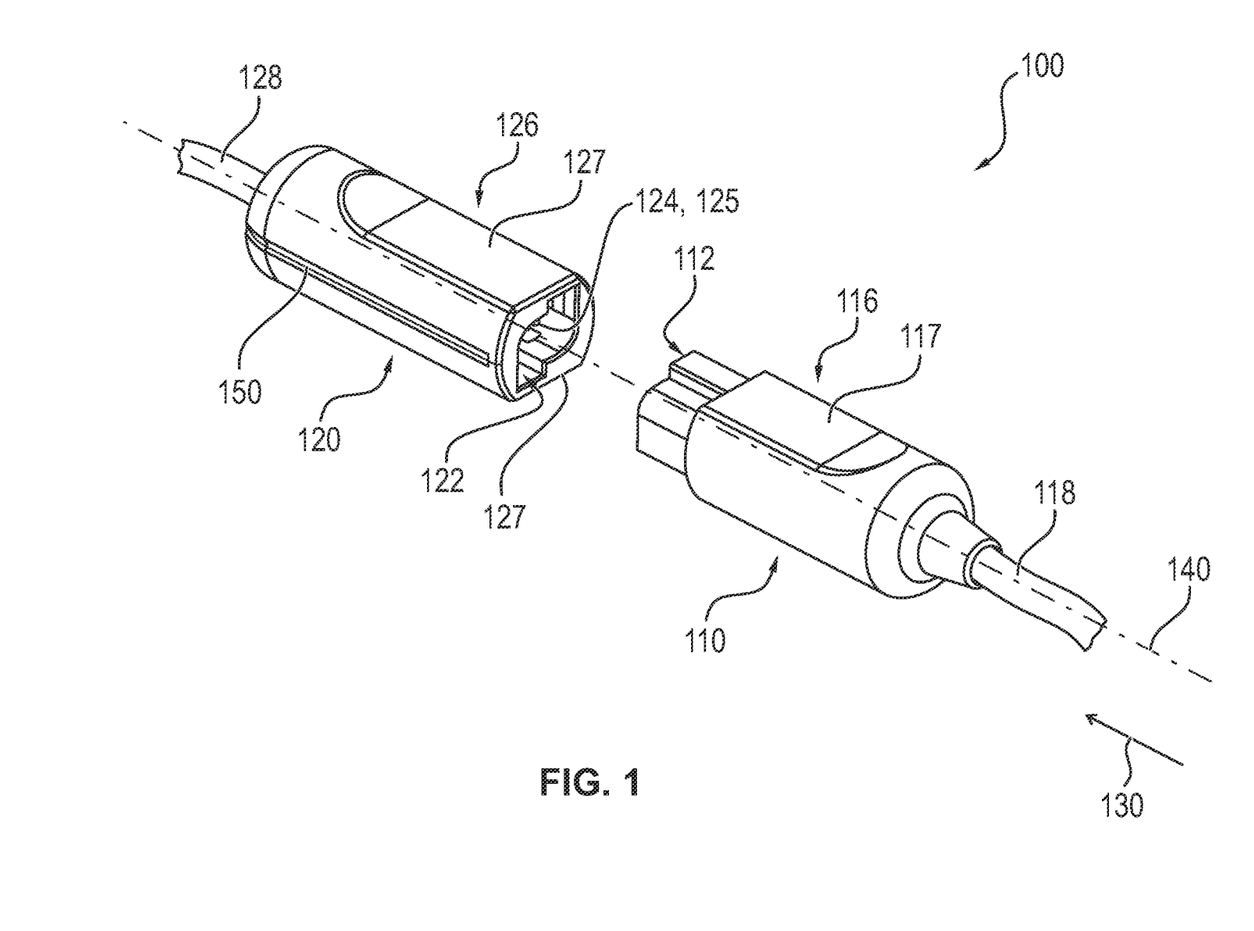
FIG. 1 is a schematic perspective view of a first exemplary embodiment of an electrical plug-in connection according to a first aspect of the present invention.

Referring to the drawings, FIG. 1 shows a schematic view of a first exemplary embodiment of an electrical plug-in connection 100 according to a first aspect of the present invention.

The electrical plug-in connection 100 is configured for the positive-locking connection of a plug-in element 110 to a receiving element 120 within a medical device arrangement.

The plug-in element 110 forms a male part of the electrical plug-in connection 100 with an insertion area 112, which has a contact element (not shown in FIG. 1) for providing an electrical connection to a corresponding contact counter element 124 of the receiving element 120. The plug-in element 110 has, furthermore, a plug-side grip area 116, which comprises two flattened areas 117 located opposite one another. A plug-side cable 118 is connected to the plug-in element 110.

Figure 2:
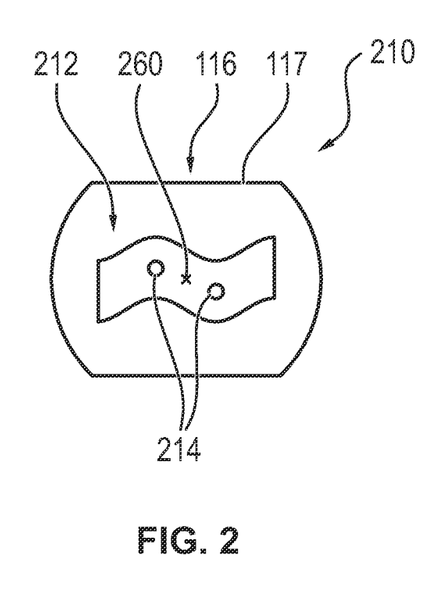
FIG. 2 is a schematic end view of one of three different exemplary embodiments of a wave-shaped insertion area of the electrical plug-in connection according to the first aspect of the present invention.
Figure 3:
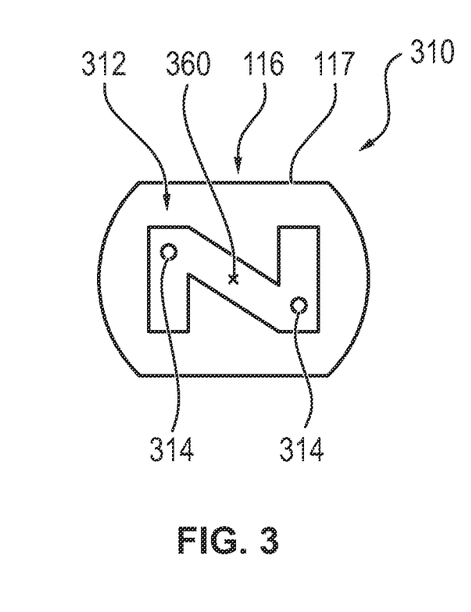
FIG. 3 is a schematic end view of another of three different exemplary embodiments of a z-shaped insertion area of the electrical plug-in connection according to the first aspect of the present invention.
Figure 4:
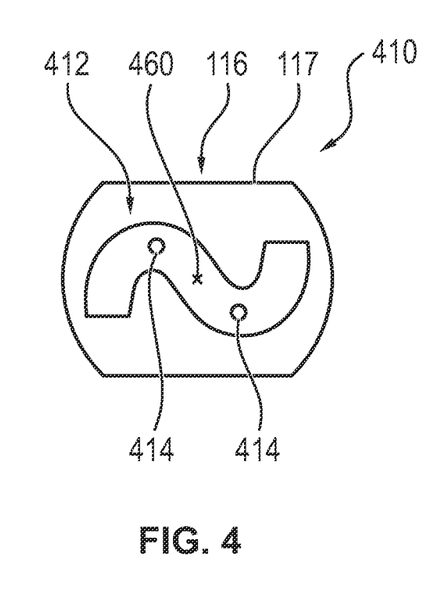
FIG. 4 is a schematic end view of another of three different exemplary embodiments of an s-shaped insertion area of the electrical plug-in connection according to the first aspect of the present invention.

The receiving element 120 forms a female part of the electrical plug-in connection 100 with a receptacle 122 corresponding to the insertion area 112. The receiving element 120 comprises the contact counter element 124, which is configured as a contact pin 125 in the present case, while the contact element of the plug-in element 110 has a contact receptacle. In the plugged-together state, the contact pin and the contact receptacle form at least two contact areas, via which an electrical connection is provided between the plug-side cable 118 and a receptacle-side cable 128 connected to the receiving element 120. The at least two contact areas are preferably provided by at least two contact pins, as shown in FIGS. 2 through 4. The receiving element 120 has, furthermore, a receptacle-side grip area 126, which likewise comprises two flattened areas 127 located opposite one another. The two grip areas 116, 126 are coordinated with one another such that a suitable angular position of the plug-in element 110 and of the receiving element 120 to one another is found intuitively by the respective flattened areas 117, 127 being brought together.

The insertion direction 130 is predetermined by the direction, into which the plug-in element 110 has to be brought in order to be inserted into the receiving element 120.

The insertion area 112 is configured as rotationally symmetrical by 180° in relation to an insertion axis 140 of the electrical plug-in connection 100, which insertion axis is oriented according to the insertion direction 130. In the exemplary embodiment being shown, the rotationally symmetrical structure of the insertion area 112 is embodied by the essentially z-shaped insertion area 112. Other shapes of the insertion area are also possible according to the present invention, as shown in FIGS. 2 through 4. A pole reversal of the electrical plug-in connection is allowed due to the rotational symmetry, as a result of which a rapid plugging together of the electrical plug-in connection 100 according to the present invention is possible. According to the present invention, the insertion area 112 and thus also the corresponding receptacle 122 are, however, not mirror symmetrical in relation to any desired reference plane comprising the insertion axis 140. Due to this characteristic structure of the insertion area 112, an accidental plugging together of unrelated pairs of plugs and receptacles can be avoided. In particular, an accidental plugging together with known, commercially available plugs, which are typically configured to allow a pole reversal in a mirror-symmetrical manner, can be avoided.

In the exemplary embodiment shown, it is especially advantageous that a bringing together of the angular positions of the flattened areas 117, 127 of the plug-in element 110 and of the receiving element 120 may always lead to a constellation in which the insertion area 112 can be inserted into the receptacle 122 because of the 180° rotational symmetry of the insertion area 112.

Furthermore, it is shown in FIG. 1 that the sheathing of the receiving element 120 of the electrical plug-in connection 100 in the exemplary embodiment shown is provided by two half shells made of plastic. The two half shells are preferably manufactured by means of an injection molding process or the like. The two half shells may be connected to one another at a corresponding connection area 150. In the exemplary embodiment being shown, this takes place via a positive-locking connection. In the exemplary embodiment shown, the sheathing takes place, furthermore, with the two half shells only for the receiving element 120, whereas the plug-in element 110 was manufactured by injection molding of the plug-side cable 118 in a mold. As a result, the receiving element 120 can be manufactured in an especially efficient manner, which is especially advantageous if the receiving element 120 is a disposable component. In an exemplary embodiment, not shown, the sheathing of the receiving element and the plug-in element is configured by two half shells. In another exemplary embodiment, not shown, the two sheathings are manufactured by injection molding.

The precise structure of such a sheathing as well as a suitable fastening of the respective cable with this sheathing are known in the field of plug-in connections and will therefore not be explained in detail below.

FIGS. 2 through 4 show a respective schematic view of three different exemplary embodiments of the insertion area 212, 312, 412 of the electrical plug-in connection 100 according to the first aspect of the present invention. A wave-shaped insertion area 212 (FIG. 2), a z-shaped insertion area 312 (FIG. 3) and an s-shaped insertion area 412 (FIG. 4) are shown here.

The three structures shown for the insertion area 212, 312, 412 are only examples of a plurality of possible structures, which are configured as rotationally symmetrical by 180°, i.e., are configured as point symmetrical as well, in the sense of the present invention, without in the process being mirror symmetrical in relation to any desired reference plane oriented corresponding to the insertion axis.

The point of intersection, at which the insertion axis intersects the corresponding insertion area 212, 312, 412, is identified by a cross 260, 360, 460 in FIGS. 2 through 4.

Furthermore, in the three exemplary embodiments shown in FIGS. 2 through 4, the sheathing of the respective plug-in element 210, 310, 410 is configured in a similar manner with two areas 117 located opposite one another, which form the respective grip area 116. Finally, each of the three insertion areas 212, 312, 412 has two contact elements 214, 314, 414, which show that the corresponding contact pins of the corresponding receiving element, which contacts pins are not shown and are located opposite one another, are arranged outside of the insertion axis.

In one exemplary embodiment, not shown, the electrical plug-in connection according to the present invention has more than two contact counter elements and/or more than two contact elements, especially contact pins.

In another exemplary embodiment, not shown, the grip area of the plug-in element and/or of the receiving element has an especially ergonomic structure, which is different from the flattened area 117 shown.

Figure 5:
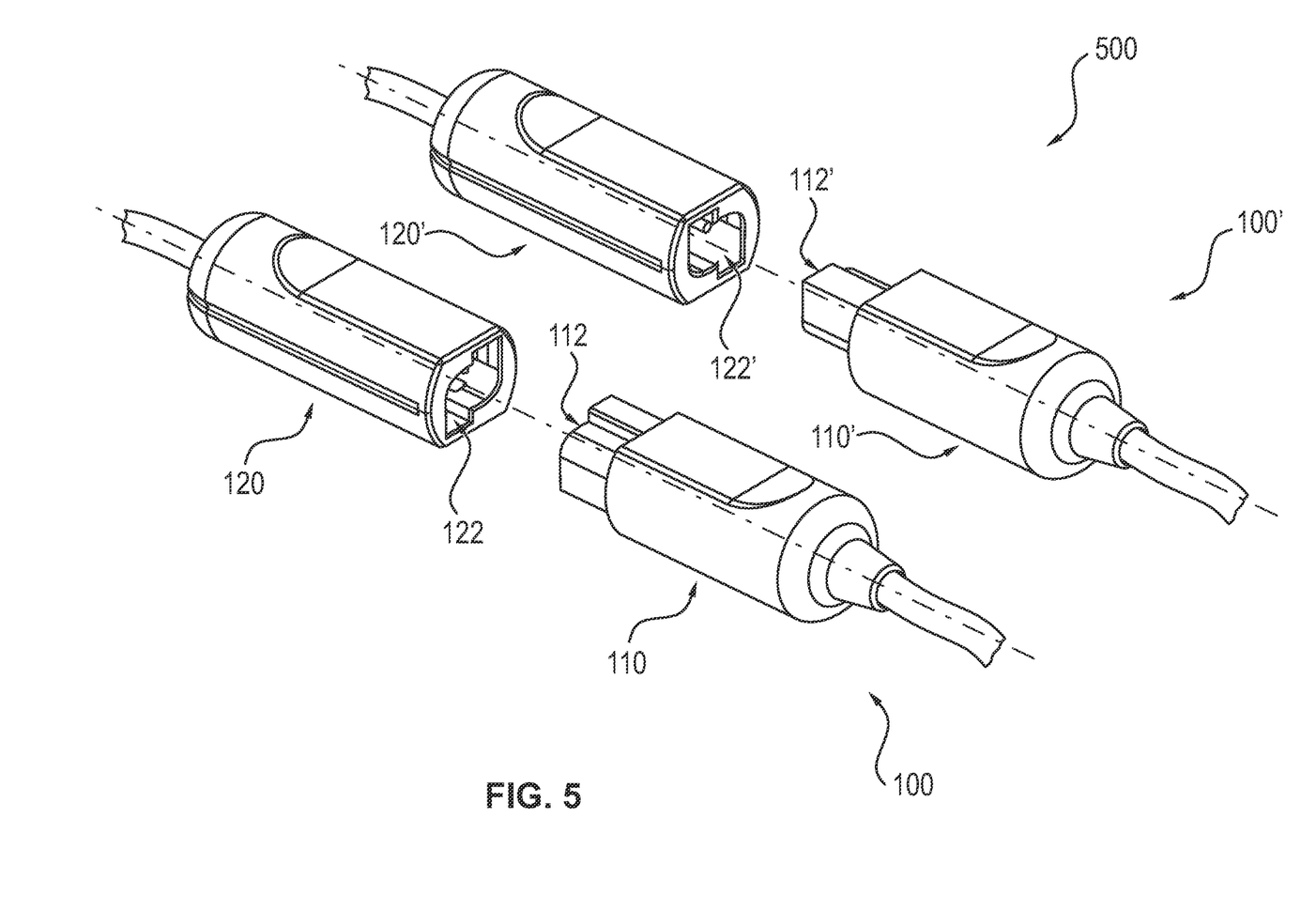
FIG. 5 is a schematic perspective view of a first exemplary embodiment of an electrical plug-in connection system according to a second aspect of the present invention.

FIG. 5 shows a schematic view of a first exemplary embodiment of an electrical plug-in connection system 500 according to a second aspect of the present invention.

The electrical plug-in connection system 500 comprises at least two electrical plug-in connections 100, 100' according to the first aspect of the present invention. The electrical plug-in connection 100' differs from the electrical plug-in connection 100 only by the insertion area 112' and by the corresponding receptacle 122' being mirrored, i.e., mirror-inverted, compared to the insertion area 112 and to the corresponding receptacle 122. Because of the non-mirror-symmetrical structure of the insertion area 112, 112' and of the receptacle 122, 122', the second receptacle 122' cannot therefore be combined with the first insertion area 112, and vice versa the first receptacle 122 also cannot be combined with the second insertion area 112'.

Otherwise, the two electrical plug-in connections 100, 100' have the same configuration and thus the same structural features.

Figure 6:
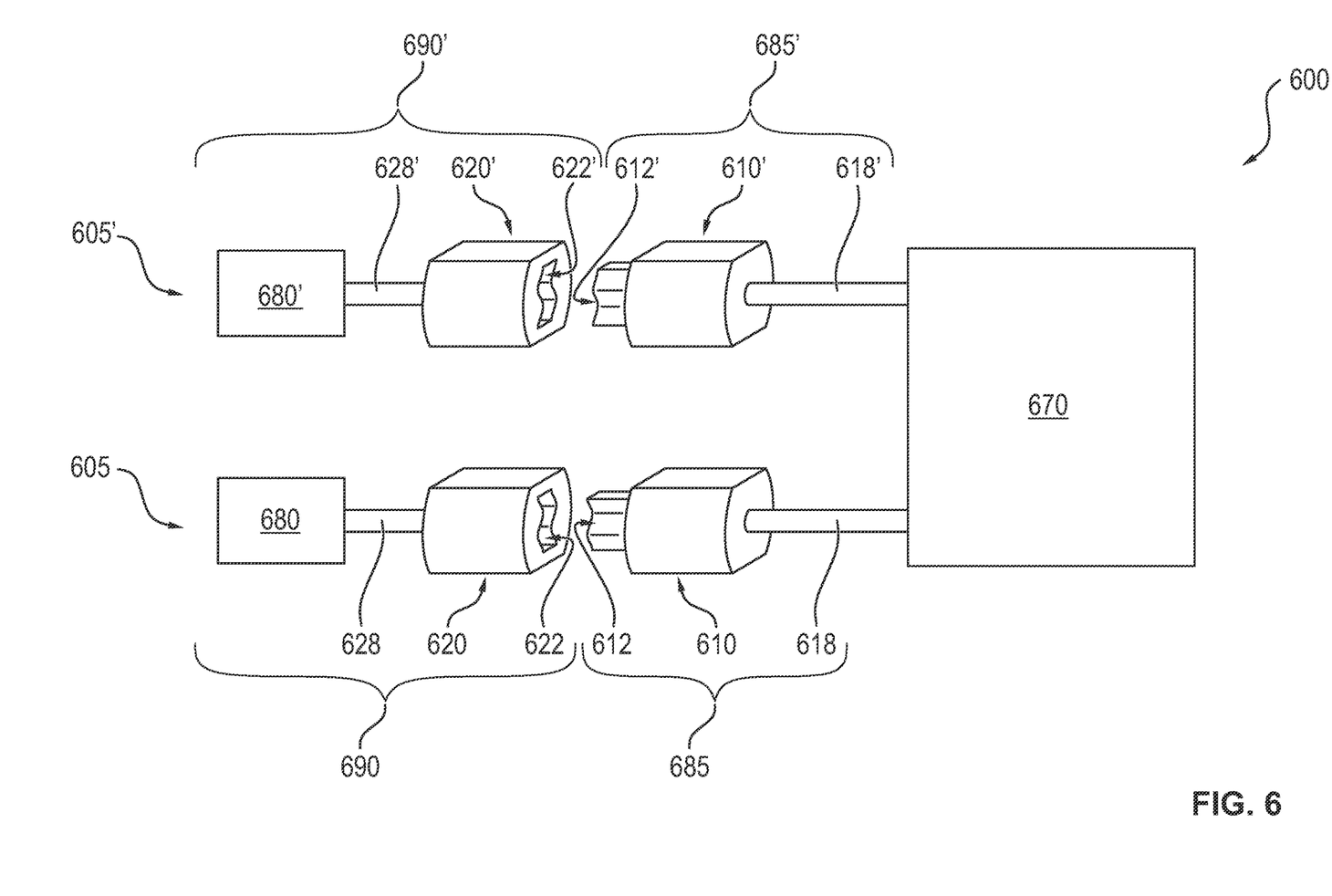
FIG. 6 is a schematic perspective view of a second exemplary embodiment of the electrical plug-in connection system according to the second aspect of the present invention.

FIG. 6 shows a schematic view of a second exemplary embodiment of the electrical plug-in connection system 600 according to the second aspect of the present invention.

The electrical plug-in connection system 600 differs from the plug-in connection system 500 shown in FIG. 5 by the two insertion areas 612, 612' and the two corresponding receptacles 622, 622' not being z-shaped as in case of the plug-in connection system 500, but rather wave-shaped. According to the present invention, the two wave shapes of the receptacles 622, 622' shown are wave shapes mirrored to one another. As a result, the receptacles and the insertion areas cannot be mixed up with one another.

Furthermore, the electrical plug-in connection system 600 differs from the plug-in connection system 500 by the plug-side cables 618, 618' being configured each to connect the electrical plug-in connection system 600 to a power supply unit 670, and the receptacle-side cables 628, 628' being configured each to connect the electrical plug-in connection system 600 to a device 680, 680' to be supplied with current. In the exemplary embodiment being shown, the two devices 680, 680' to be supplied with power are medical devices, and especially a respective heating element of a medical device.

Finally, the two plug-in elements 610, 610' together with the plug-side cables (618, 618') are reusable components (685, 685'), while the two receiving elements 620, 620' are disposable components. In the exemplary embodiment shown, the two receiving elements 620, 620' together with the two receptacle-side cables 628, 628' and with the two medical devices 680, 680' are combined disposable components 690, 690'.

The color configuration of the electrical plug-in connection system 600 is not shown in FIG. 6. Thus, the plug-in element 610 and the receiving element 620 of the first electrical plug-in connection 605 are provided in a first color and the plug-in element 610' as well as the receiving element 620' of the second electrical plug-in connection 605' are provided in a second color, wherein the two colors are different.

Figure 7:
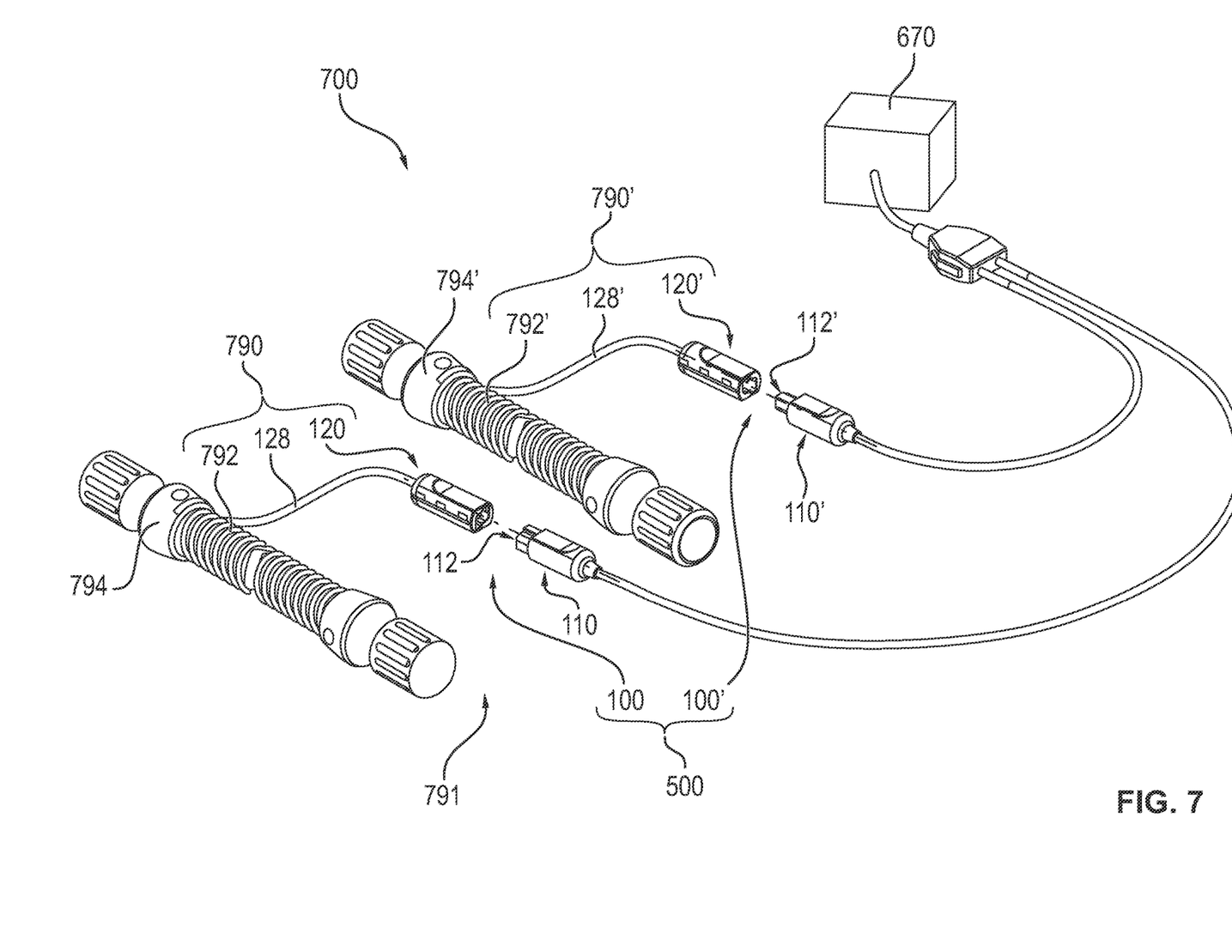
FIG. 7 is a schematic perspective view of an exemplary embodiment of a medical device arrangement according to a third aspect of the present invention.

FIG. 7 shows a schematic view of an exemplary embodiment of a medical device arrangement 700 according to the third aspect of the present invention.

The medical device arrangement 700 according to the present invention comprises the electrical plug-in connection system 500 according to the present invention according to the second aspect of the present invention.

In addition to the components according to the present invention of the electrical plug-in connection system 500, the medical device arrangement 700 in the exemplary embodiment shown comprises a heatable tube system 791, which is to be supplied with power by the power supply unit 670 via the electrical plug-in connection system 500. In this case, a respective plug-in connection 110, 110' is associated with a respective heatable tube 792, 792' of the tube system of the medical device arrangement 700.

Via the respective plug-in connection, a respective heater 794, 794' of the corresponding heatable tube 792, 792', especially a heater of a breathing gas humidifier in the present case, is supplied with power.

In the exemplary embodiment shown in FIG. 7, the two heatable tubes 792,792' are an inspiratory ventilation tube 792 and an expiratory ventilation tube 792'. Since the inspiratory heating voltage is controlled electrically in the present case and the expiratory heating voltage is not, a mix-up of the plug-in elements 110, 110' with one another must be avoided for reasons of patient safety. Due to the characteristic structure of the respective insertion area according to the present invention, in which the two electrical plug-in connections 100, 100' have insertion areas 112, 112' mirrored to one another, a mix-up of the plug-in elements 110, 110' cannot advantageously take place.

Furthermore, in the exemplary embodiment shown, the respective receiving element 120, 120' is non-detachably connected to the associated heatable tube 792, 792' via the respective receptacle-side cable 128, 128'. In this case, a respective combination of the receiving element 120, 120', the receptacle-side cable 128, 128' and the heatable tube 792,792' together form a combined disposable component 790, 790' of the medical device arrangement.

The electrical plug-in connection according to the present invention according to the first aspect of the present invention may, of course, be advantageously used in other exemplary embodiments, not shown, for other medical devices and/or medical components. Especially for a medical device arrangement, which has two elements to be supplied with power, the electrical connections of which must not be mixed up, such a mix-up can especially advantageously be prevented. In such an application, patient safety is supported and handling of the corresponding plug-in connection by the user is simplified by the electrical plug-in connection according to the first aspect of the present invention and/or the electrical plug-in connection system according to the second aspect of the present invention.

While specific embodiments of the invention have been shown and described in detail to illustrate the application of the principles of the invention, it will be understood that the invention may be embodied otherwise without departing from such principles.

LIST OF REFERENCE NUMBERS 100, 100', 605, 605' Electrical plug-in connection
110, 110', 210, 310, 410, Plug-in element
610, 610'
112, 112', 212, 312, 412, Insertion area
612, 612'
116, 126 Grip area
117, 127 Flattened area
118, 618, 618' Plug-side cable
120, 120', 620, 620' Receiving element
122, 122', 622, 622' Receptacle
124 Contact counter element
125 Contact pin
128, 128', 628, 628' Receptacle-side cable
130 Insertion direction
140 Insertion axis
150 Connection area
214, 314, 414 Contact element
260, 360, 460 Point of intersection
500, 600 Electrical plug-in connection system
670 Power supply unit
680, 680' Device to be supplied
685, 685' Reusable component
690, 690', 790, 790' Combined disposable component 700 Medical device arrangement
791 Tube system
792, 792' Tube
794, 794' Heater

What is claimed is:

1. An electrical plug-in connection comprising:
a plug-in element forming a male part of the electrical plug-in connection, with an insertion area;
a receiving element forming a female part of the electrical plug-in connection, with a receptacle corresponding to the insertion area, to provide a positive connection of the plug-in element to the receiving element within a medical device arrangement, wherein:
the plug-in element and the receiving element are configured to provide an electrical connection between a plug-side cable connected to the plug-in element and a receptacle-side cable connected to the receiving element, in a plugged-together state, via at least two contact areas;
the insertion area is configured to be rotationally symmetrical by 180° in relation to an insertion axis of the electrical plug-in connection and the insertion axis is oriented according to an insertion direction whereby there may be a pole reversal of the electrical plug-in connection and the insertion area is configured to not be mirror symmetrical in relation to a reference plane comprising the insertion axis; and
the insertion area has an essentially wave-shaped, z-shaped or s-shaped configuration.

2. An electrical plug-in connection in accordance with claim 1, wherein each of the two contact areas comprise a contact pin to provide two contact pins arranged outside of the insertion axis.

3. An electrical plug-in connection system comprising:
a first electrical plug-in connection comprising a first plug-in element forming a male part of the first electrical plug-in connection, with a first insertion area, a first receiving element forming a female part of the first electrical plug-in connection, with a first receptacle corresponding to the first insertion area, to provide a positive connection of the first plug-in element to the first receiving element within a medical device arrangement, wherein the first plug-in element and the first receiving element are configured to provide an electrical connection between a first plug-side cable connected to the first plug-in element and a first receptacle-side cable connected to the first receiving element, in a plugged-together state, via at least two first connection contact areas, the first insertion area is configured to be rotationally symmetrical by 180° in relation to a first insertion axis of the first electrical plug-in connection and the first insertion axis is oriented according to a first insertion direction, whereby there may be a pole reversal of the first electrical plug-in connection and the first insertion area is configured to not be mirror symmetrical in relation to a reference plane comprising the insertion axis and the first insertion area has an essentially wave-shaped, z-shaped or s-shaped configuration;
a second electrical plug-in connection comprising a second plug-in element forming a male part of the second electrical plug-in connection, with a second insertion area, a second receiving element forming a female part of the second electrical plug-in connection, with a second receptacle corresponding to the second insertion area, to provide a positive connection of the second plug-in element to the second receiving element within a medical device arrangement, wherein the second plug-in element and the second receiving element are configured to provide an electrical connection between a second plug-side cable connected to the second plug-in element and a second receptacle-side cable connected to the second receiving element, in a plugged-together state, via at least two second connection contact areas, the second insertion area is configured to be rotationally symmetrical by 180° in relation to a second insertion axis of the second electrical plug-in connection and the second insertion axis is oriented according to a second insertion direction, whereby there may be a pole reversal of the second electrical plug-in connection and the second insertion area is configured to not be mirror symmetrical in relation to a reference plane comprising the insertion axis and the second insertion area has an essentially wave-shaped, z-shaped or s-shaped configuration, wherein:
the first insertion area of the first electrical plug-in connection is mirror-inverted relative to the second insertion area of the second electrical plug-in connection.

4. An electrical plug-in connection system in accordance with claim 3, wherein:
the first plug-in element with the first side cable and the second plug-in element with the second side cable form reusable components; and
the first receiving element with the first receptacle-side cable and the second receiving element with the second receptacle-side cable form disposable components of the electrical plug-in connection system.

5. An electrical plug-in connection system in accordance with claim 3, wherein:
each of the first plug-side cable and the second plug side cable are configured to connect the electrical plug-in connection system to a power supply unit; and
each of the first receptacle-side cable and the second receptacle-side cable are configured to connect the electrical plug-in connection system to a respective device to be supplied with power.

6. An electrical plug-in connection system in accordance with claim 3, wherein:
the first plug-in element and the first receiving element of the first electrical plug-in connection are at least partially configured in a first color; and
the second plug-in element and the second receiving element of the second electrical plug-in connection are at least partially configured in a second color;
the first color and the second color are different from one another.

7. An electrical plug-in connection system in accordance with claim 1, wherein each of the two contact areas comprise a contact pin to provide two contact pins arranged outside of the insertion axis.

8. A medical device arrangement comprising an electrical plug-in connection system comprising:
a first electrical plug-in connection comprising a first plug-in element forming a male part of the first electrical plug-in connection with a first insertion area, a first receiving element forming a female part of the first electrical plug-in connection with a first receptacle corresponding to the first insertion area to provide a connection of the first plug-in element to the first receiving element within a medical device arrangement, wherein the first plug-in element and the first receiving element are configured to provide an electrical connection between a first plug-side cable connected to the first plug-in element and a first receptacle-side cable connected to the first receiving element, in a plugged-together state, via at least two first connection contact areas, the first insertion area is configured to be rotationally symmetrical by 180° in relation to a first insertion axis of the first electrical plug-in connection and the first insertion axis is oriented according to a first insertion direction, whereby there may be a pole reversal of the first electrical plug-in connection and the first insertion area is configured to not be mirror symmetrical in relation to a reference plane comprising the insertion axis and the first insertion area has an essentially wave-shaped, z-shaped or s-shaped configuration; and a second electrical plug-in connection comprising a second plug-in element forming a male part of the second electrical plug-in connection with a second insertion area, a second receiving element forming a female part of the second electrical plug-in connection with a second receptacle corresponding to the second insertion area to provide a connection of the second plug-in element to the second receiving element within a medical device arrangement, wherein the second plug-in element and the second receiving element are configured to provide an electrical connection between a second plug-side cable connected to the second plug-in element and a second receptacle-side cable connected to the second receiving element, in a plugged-together state, via at least two second connection contact areas, the second insertion area is configured to be rotationally symmetrical by 180° in relation to a second insertion axis of the second electrical plug-in connection and the second insertion axis is oriented according to a second insertion direction, whereby there may be a pole reversal of the second electrical plug-in connection and the second insertion area is configured to not be mirror symmetrical in relation to a reference plane comprising the insertion axis and the second insertion area has an essentially wave-shaped, z-shaped or s-shaped configuration, wherein:

the first insertion area of the first electrical plug-in connection is mirror-inverted relative to the second insertion area of the second electrical plug-in connection.

9. A medical device arrangement in accordance with claim 8, further comprising a tube system, the tube system comprising:

a first heatable tube and wherein the first heatable tube comprises a first heater supplied with power via the first plug-in connection; and a second heatable tube and wherein the second heatable tube comprises a second heater supplied with power via the first plug-in connection.

10. A medical device arrangement in accordance with claim 9, wherein:

the first receiving element is connected non-detachably to the first heatable tube via the first receptacle-side cable;

the second receiving element is connected non-detachably to the second heatable tube via the second receptacle-side cable;

the first receiving element, the first receptacle-side cable and the first heatable tube together form a disposable component of the medical device arrangement.

11. A medical device arrangement in accordance with claim 8, wherein:

the first plug-in element with the first side cable and the second plug-in element with the second side cable form reusable components; and the first receiving element with the first receptacle-side cable and the second receiving element with the second receptacle-side cable form disposable components of the electrical plug-in connection system.

12. A medical device arrangement in accordance with claim 8, further comprising:

a power supply unit;

a first power consuming device; and a second power consuming device, wherein:

each of the first plug-side cable and the second plug side cable are configured to connect the electrical plug-in connection system to the power supply unit; and each of the first receptacle-side cable and receptacle-side cable are configured to connect the electrical plug-in connection system to one of the first power consuming device and the second power consuming device.

13. A medical device arrangement in accordance with claim 8, wherein:

the first plug-in element and the first receiving element of the first electrical plug-in connection are at least partially configured in a first color; and the second plug-in element and the second receiving element of the second electrical plug-in connection are at least partially configured in a second color;

the first color and the second color are different from one another.

14. A medical device arrangement in accordance with claim 8, wherein each of the two contact areas comprise a contact pin to provide two contact pins arranged outside of the insertion axis.

* * * * *